United States Patent
Lin

(10) Patent No.: US 8,366,444 B2
(45) Date of Patent: Feb. 5, 2013

(54) ARTIFICIAL TOOTH WITH MULTIPLE INTERNAL CROWNS

(76) Inventor: Tai-Wu Lin, Taipei (TW)

(*) Notice: Subject to any disclaimer, the term of this patent is extended or adjusted under 35 U.S.C. 154(b) by 0 days.

(21) Appl. No.: 13/104,953

(22) Filed: May 10, 2011

(65) Prior Publication Data

US 2012/0178050 A1 Jul. 12, 2012

(30) Foreign Application Priority Data

Jan. 10, 2011 (TW) .............................. 10200456 U

(51) Int. Cl.
*A61C 13/10* (2006.01)

(52) U.S. Cl. ......................................................... 433/193

(58) Field of Classification Search .......... 433/191–194, 433/204, 211, 218–221, 172
See application file for complete search history.

(56) References Cited

U.S. PATENT DOCUMENTS

| | | | | |
|---|---|---|---|---|
| 1,753,644 A * | 4/1930 | Burden | ......................... | 433/181 |
| 2,194,790 A * | 3/1940 | Gluck | ........................... | 433/183 |
| 2,826,814 A * | 3/1958 | Sappey et al. | ................. | 433/193 |
| 3,430,344 A * | 3/1969 | Sekendur | ..................... | 433/219 |
| 3,434,209 A * | 3/1969 | Weissman | .................... | 433/225 |
| 3,656,236 A * | 4/1972 | Kurer | ............................ | 433/221 |
| 3,675,328 A * | 7/1972 | Weissman | .................... | 433/225 |
| 3,675,329 A * | 7/1972 | Weissman | ...................... | 433/225 |
| 3,797,114 A * | 3/1974 | Wiland | ......................... | 433/219 |
| 3,962,787 A * | 6/1976 | Corbett | ........................ | 433/220 |
| 4,500,296 A * | 2/1985 | Friedman | ...................... | 433/225 |
| 4,627,136 A * | 12/1986 | Kreylos et al. | ............... | 29/896.1 |
| 5,030,094 A * | 7/1991 | Nardi et al. | ................... | 433/169 |
| 5,221,206 A * | 6/1993 | Nardi | ............................. | 433/193 |
| 5,575,651 A * | 11/1996 | Weissman | ...................... | 433/173 |
| 5,613,854 A * | 3/1997 | Sweatt | ......................... | 433/223 |
| 5,782,245 A * | 7/1998 | Divjak | ......................... | 128/898 |
| 5,803,737 A * | 9/1998 | Lyalin | .......................... | 433/223 |
| 6,450,815 B1 * | 9/2002 | Weisman | ...................... | 433/220 |
| 7,108,511 B1 * | 9/2006 | Shatkin | ........................ | 433/174 |
| 2001/0036618 A1 * | 11/2001 | Worthington | ................. | 433/183 |
| 2004/0219490 A1 * | 11/2004 | Gartner et al. | ............... | 433/218 |
| 2005/0074725 A1 * | 4/2005 | Wu | ................................ | 433/223 |
| 2007/0105067 A1 * | 5/2007 | Hayashi et al. | ............... | 433/172 |

FOREIGN PATENT DOCUMENTS

DE        3320902 A1 *   3/1985

* cited by examiner

*Primary Examiner* — Cris L Rodriguez
*Assistant Examiner* — Matthew Saunders

(57) ABSTRACT

The present invention provides an artificial tooth with multiple internal crowns, which includes a plurality of the internal crown members, a plurality of the connection bars, and at least one external crown member. The internal crown members are respectively fit to a plurality of the abutments. Each of the connection bars connects to at least two of the internal crown members. The external crown member forms therein a plurality of recesses. The recesses are formed to correspond to the internal crown members. The external crown member, when fit to the internal crown members, forms a tight engagement with the internal crown members.

4 Claims, 11 Drawing Sheets

ARTIFICIAL TOOTH WITH MULTIPLE INTERNAL CROWNS

(a) TECHNICAL FIELD OF THE INVENTION

The present invention generally relates to an artificial tooth, and more particularly to an artificial tooth having multiple tooth-root internal crowns.

(b) DESCRIPTION OF THE PRIOR ART

An artificial tooth is used to rebuild a damage tooth of a patient in order to maintain normal function of mastication of the patient and to keep the tooth again subsequent corrosion.

A known structure of artificial tooth that is currently available is composed of internal and external crown members, wherein the internal crown is mounted to a natural tooth and then the external crown is fit to the internal crown. This arrangement allows a user to easily remove the external crown for cleaning the circumference of the tooth neck, or to replace and repair a damaged external crown without affecting regular chewing of the patient.

As shown in FIG. 1 of the attached drawings, jaw bone is located around the tooth furcation under a natural tooth 90 and food residues may get accumulated there and rotting there, causing the formation of bone-corroding rotting cavity 91 in which rotten flesh accumulates. Since the rotting cavity 91 is located at the root furcation that is surrounded by the gum, it is difficult for a dentist who attempts to perform a cleaning operation to extend a tool deeply to such a location for throughout cleaning. Further, the food residues may be hidden in a bone cavity at the furcation area that is located deeply below the gum, making it hard for daily cleaning and thus leading to subsequent corrosion of the natural tooth and the bone at the furcation area after a user wears a single-crown fixed type artificial tooth and an original German manufacturer's design of single internal crown structure. Once this get severe enough to cause pyosis and swelling and pain, besides being hard to treat the cavity in the furcation area, it is also hard to completely clean the rotting cavities in the furcation area.

SUMMARY OF THE INVENTION

In view of the above discussed problem, the present invention provides a multiple internal crown structure that is easy to clean and composed of segmented root portions or implants and that allows a dentist to completely cleaning the corroded cavities in the furcation area of the tooth root before installation of the present invention for eliminating the potential risk of subsequent corrosion.

The present invention provides an artificial tooth with multiple internal crowns, which comprises a plurality of the internal crown members, a plurality of the connection bars, and at least one external crown member. The internal crown members are respectively fit to a plurality of the abutments. Each of the connection bars connects to at least two of the internal crown members. The external crown member forms therein a plurality of recesses. The recesses are formed to correspond to the internal crown members. The external crown member, when fit to the internal crown members, forms a tight engagement with the internal crown members.

The present invention can be incorporated with a retention structure to improve the coupling of the internal and external crown members, wherein the internal crown members are respectively fit to a plurality of the abutments and each of the connection bars has two end respectively connected to two of the internal crown members. The external crown member forms therein a plurality of recesses and the recesses are formed to correspond to the internal crown members. The retention structure comprises a retention block and a resilient cap. The retention block is of a spherical form and is mounted to one of the internal crown members. The resilient cap is formed in one of the recesses. The resilient cap forms an opening and a fitting chamber. The opening and the fitting chamber are in communication with each other. The opening is formed to correspond to the retention block. The fitting chamber is fit to and encloses an outer circumference of the retention block.

As such, the present invention provides a space for easy cleaning. A patient can easily remove food residues from the teeth so as to eliminate the problems occurring in the conventional prosthetic devices. Further, before installation, a natural tooth is first cut to separate portions to allow dirt or rotten substance in the furcation area of tooth root to be completely removed. Thus, any problem caused by dirt or rotten substance after the installation of the internal crown member can be eliminated, thereby overcoming the drawbacks of the conventional prosthetic devices and also improving the convenience of daily cleaning and facilitating uniform distribution of force applied thereto. Before the present invention is made, a dentist cannot properly treat the previously discussed problems based on the state-of-the-art technology and the patient is not allowed to remove the rotten substance through daily cleaning.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

Referring to FIGS. 2-5, the present invention provides an artificial tooth with multiple internal crowns, which comprises a plurality of internal crown members 10, a plurality of the connection bars 20, and at least one external crown member 30.

The internal crown members 10 are respectively fit to a plurality of the abutments T. Each of the connection bars 20 has two ends respectively connected to at least two of the internal crown members 10 to increase a loading force that each of the internal crown members 10 may bear and to spread and reduce the magnitude of force that each unit area need to support, thereby reducing the magnitude of force that peels off and damages each bonding structure.

The external crown member 30 forms therein a plurality of the recesses 31. The recesses 31 are formed to correspond in locations to the internal crown members 10. The external crown member 30, when fit to the internal crown members 10, forms a tight engagement with the internal crown members 10 to securely couple the external crown member 30 and the internal crown members 10 together to form the artificial tooth.

Figure 1:
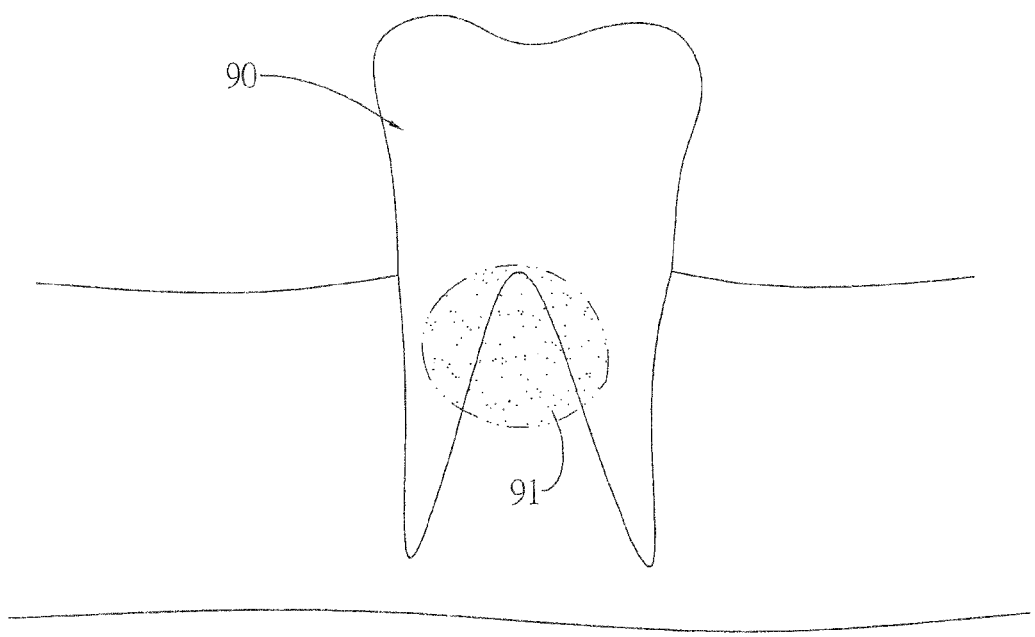
FIG. 1 is a schematic view showing dirt accumulated under a natural tooth.
Figure 2:
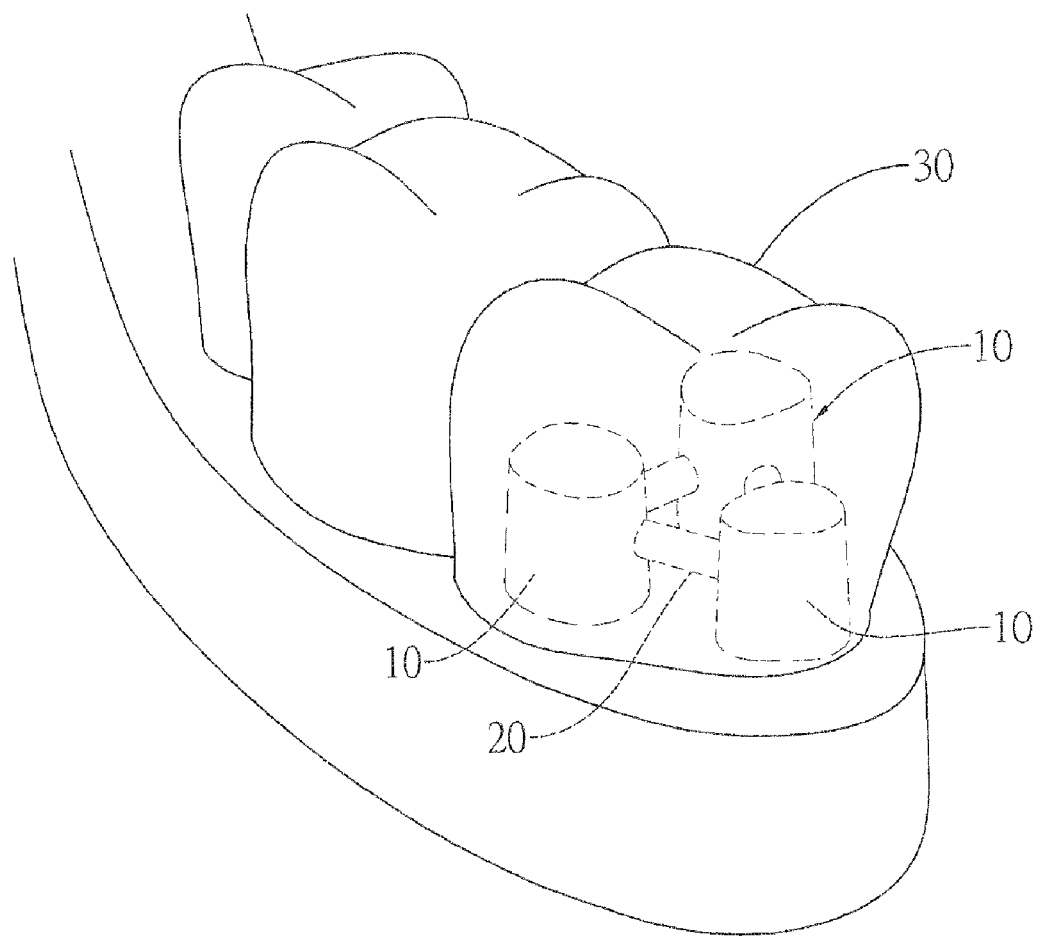
FIG. 2 is a schematic view showing an embodiment according to the present invention.
Figure 3:
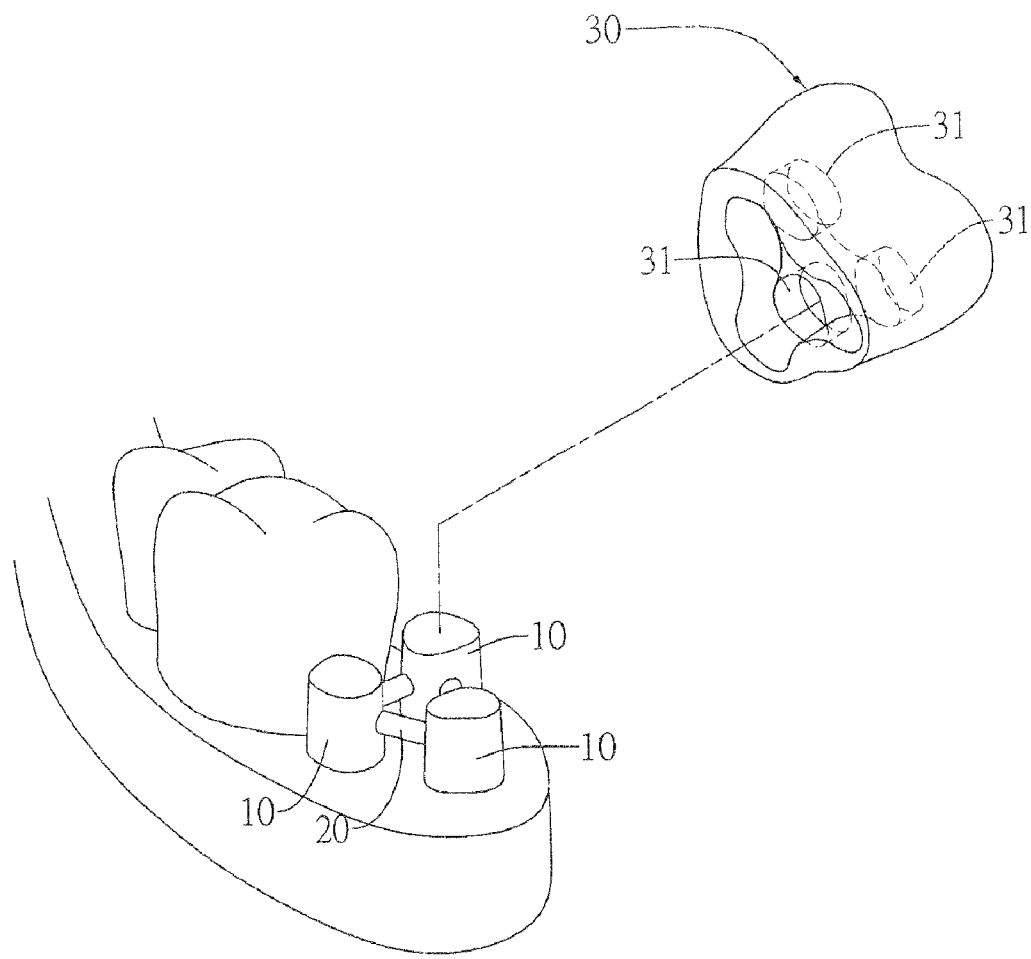
FIG. 3 is a schematic view showing spatial relationship between components of the present invention.
Figure 4:
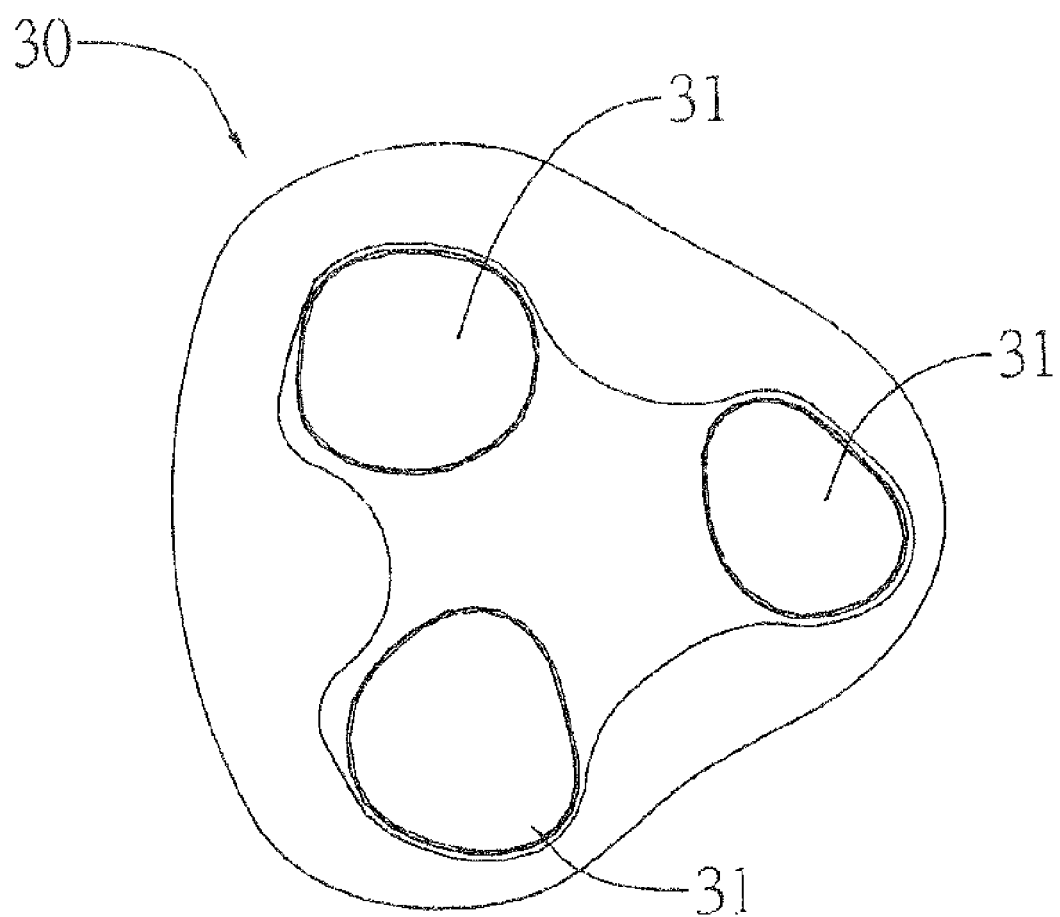
FIG. 4 is a schematic bottom view of an external crown member of the embodiment according to the present invention.
Figure 5:
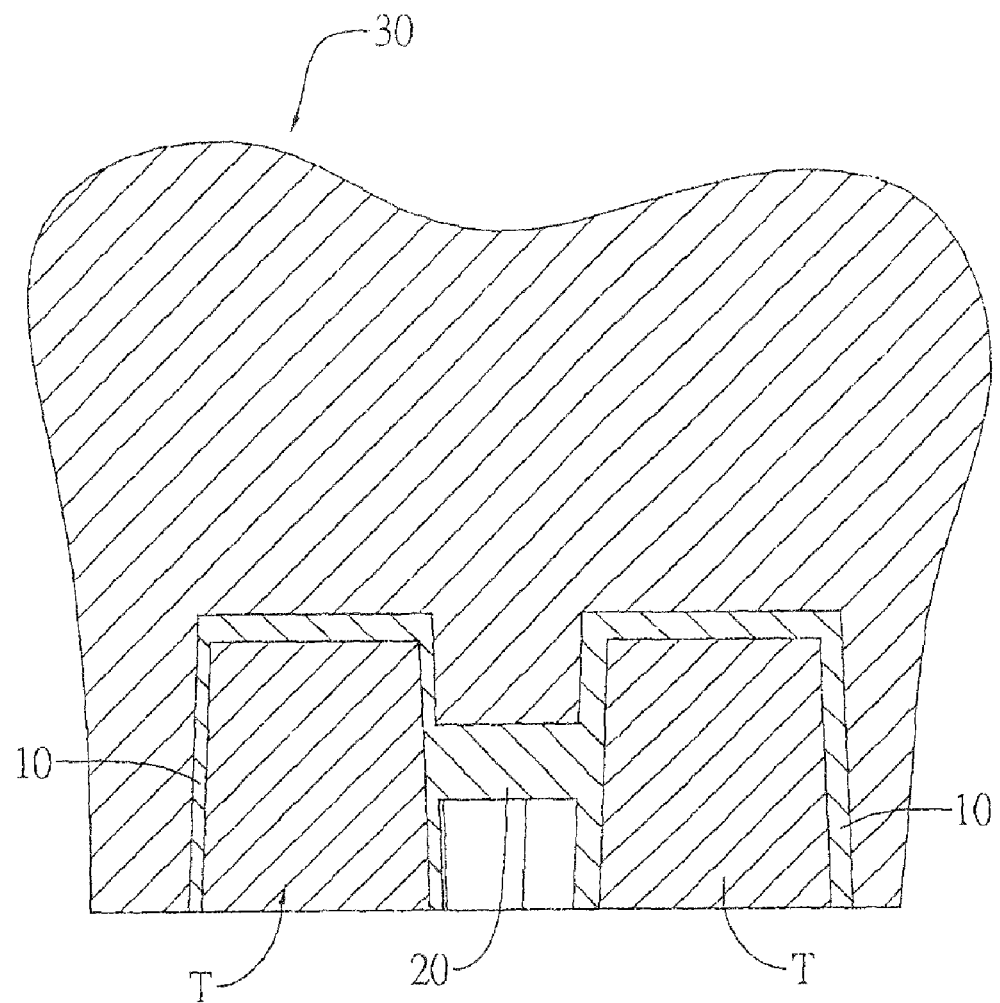
FIG. 5 is a schematic cross-sectional view of the present invention in an assembled form.

As shown in FIG. 5, the abutments T are originally a tooth, which is subjected to cutting through the crown and the root thereof so as to form an unimpeded channel for a rotting cavity in the furcation area of the root under the crown. This facilitates completely removing rotten flesh for treatment purposes and also facilitates effective cleaning by a patient without any harmful substance left in the root furcation among the abutments, and allow for inspection and identification of health and firm stability of the bone around the abutments of the internal crown members 10. Further, the abutments T may be formed by artificial implants and is not limited to cutting a natural tooth.

Since the internal crown members 10 form a sufficient space therebetween to serve as a channel, a user may easily use a cleaning tool, such as an interdental brush or a flushing device to clean off food residues between the internal crown members 10, so that no rotten substance may be left and caring or advanced treatment of the tooth can be easily performed.

Figure 6:
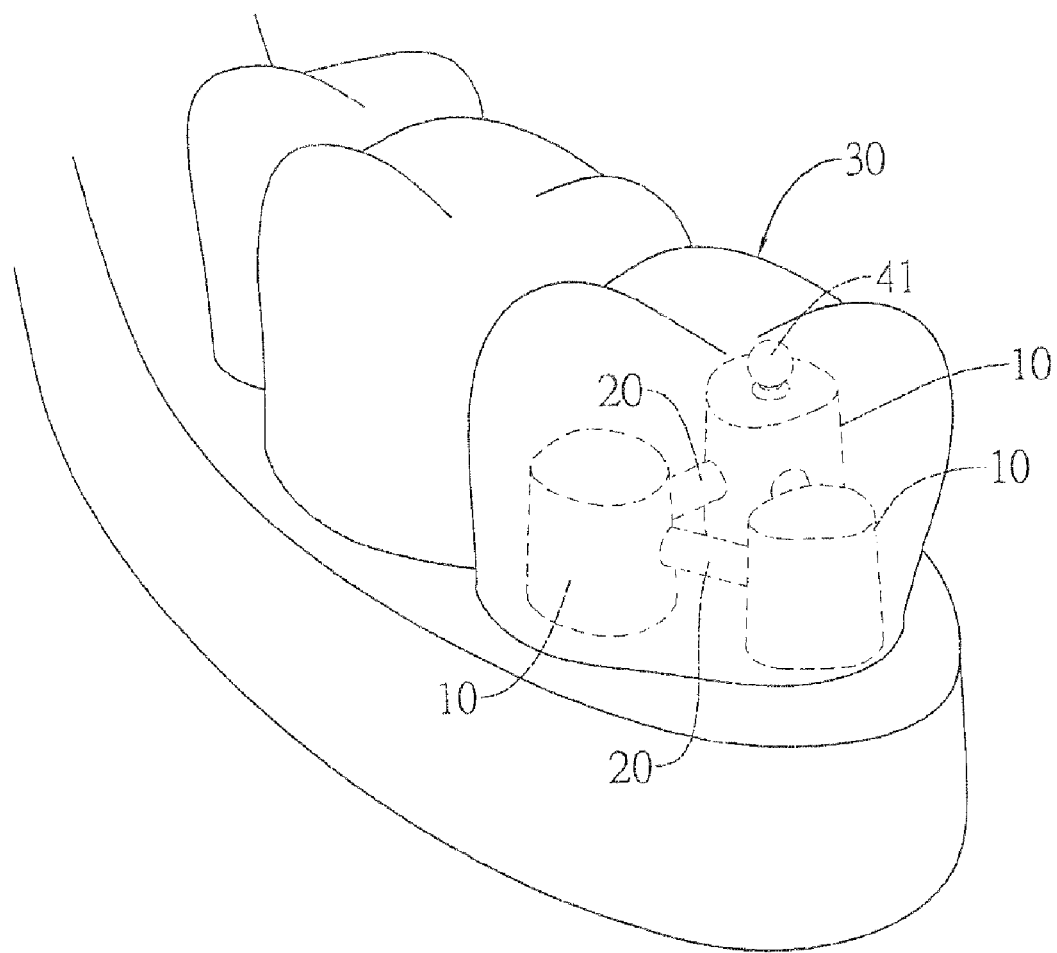
FIG. 6 is a schematic view showing a retention structure incorporated in the present invention in an assembled form.
Figure 7:
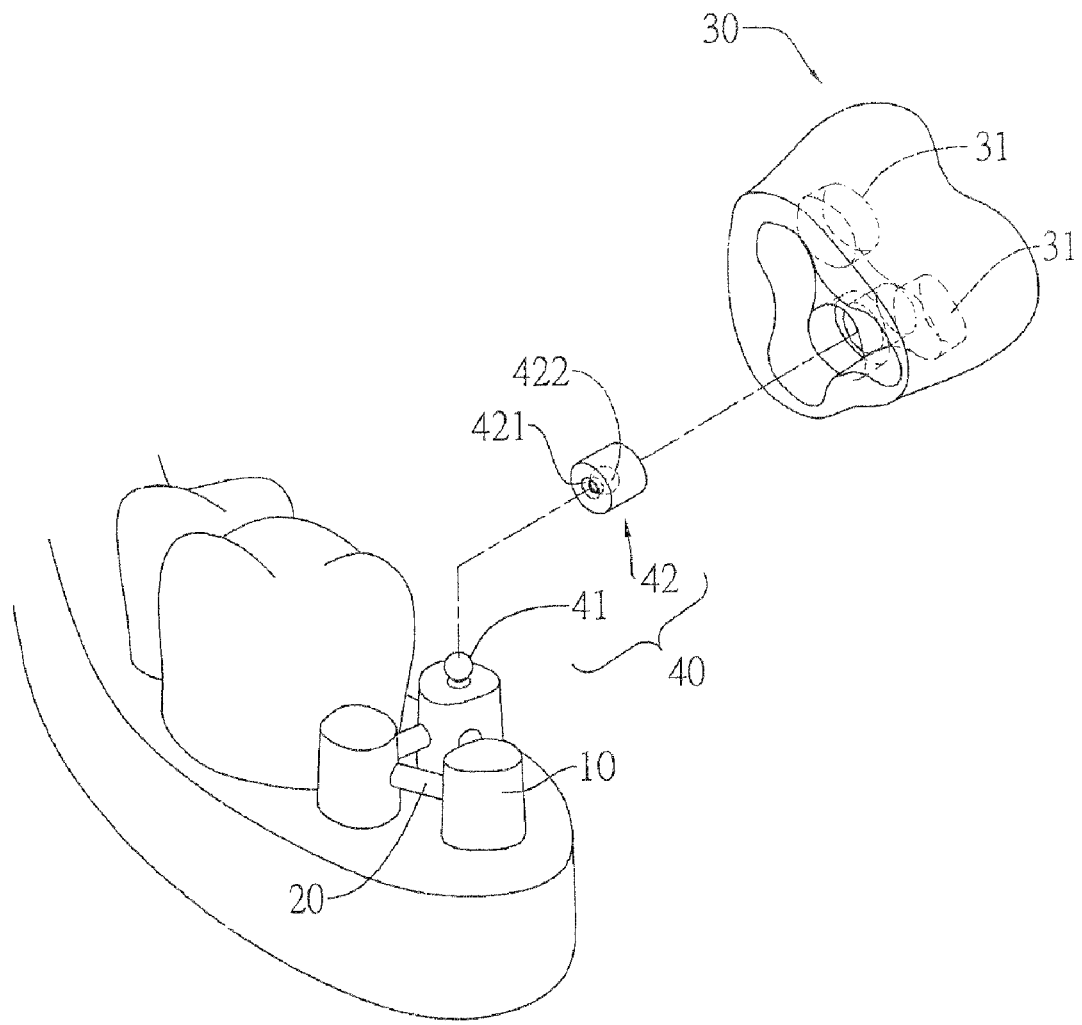
FIG. 7 is a schematic view showing the spatial relationship in mounting the retention structure according to the present invention.
Figure 8:
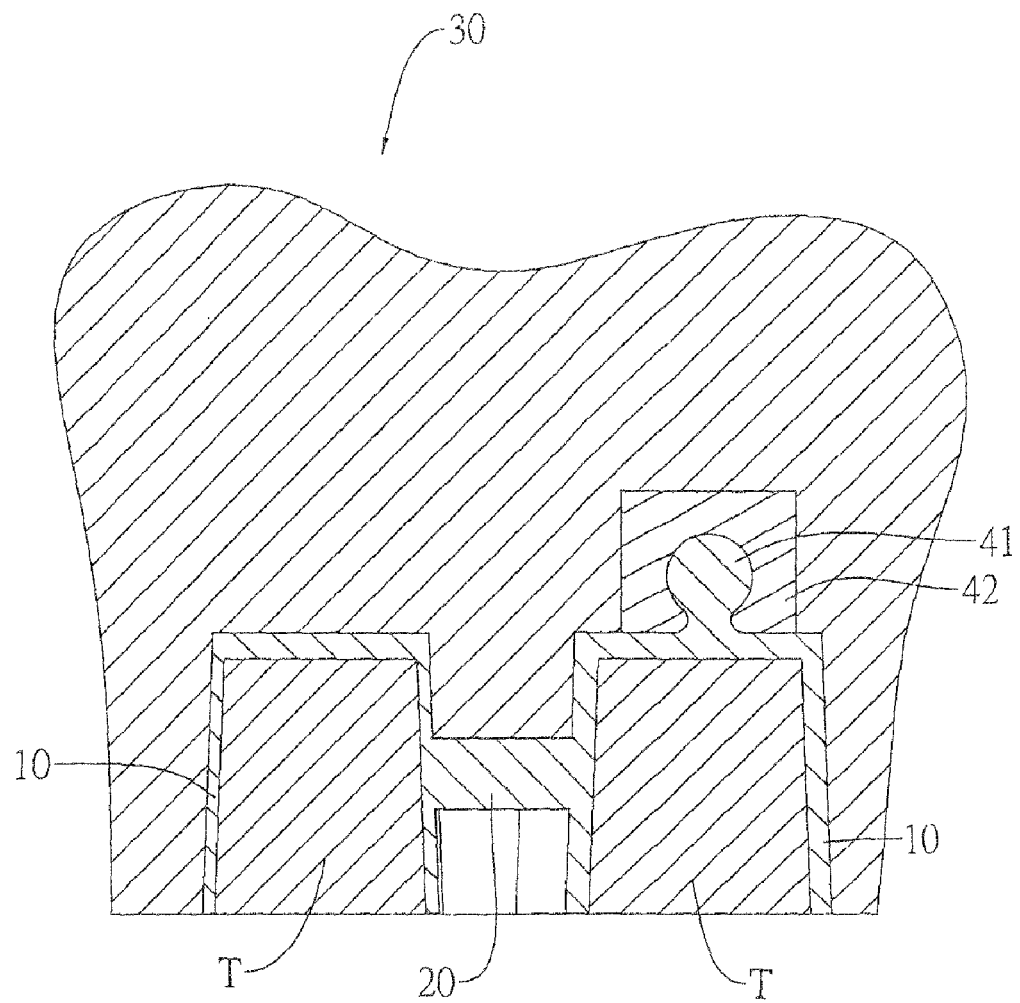
FIG. 8 is a schematic cross-sectional view showing the retention structure incorporated in the present invention.

Further, referring to FIGS. 6-8, the present invention also provides a retention structure 40 that can be used individually or in combination with the internal crown members 10 and the external crown member 30. The retention structure 40 comprises a retention block 41 and a resilient cap 42, wherein the retention block 41 is of a spherical form and is mounted to one of the internal crown members 10. The resilient cap 42 is mounted inside one of the recesses 31 and comprises an opening 421 and a fitting chamber 422. The opening 421 and the fitting chamber 422 are in communication with each other. The opening 421 is formed to correspond to the retention block 41 and is smaller than a maximum outside diameter of the retention block 41. The fitting chamber 422 can be fit over and thus encloses an outer circumference of the retention block 41 to form a clamping engagement.

When the external crown member 30 is fit to the internal crown members 10, the opening 421 of the resilient cap 42 is first positioned on the retention block 41. With the external crown member 30 being further depressed toward the internal crown members 10, the opening 421 is expanded to allow the retention block 41 to slide into the resilient cap 42, whereby the resilient cap 42 encloses an clamps the retention block 41 to form the clamping engagement and the internal crown members 10 and the external crown member 30 are thus securely coupled together.

To remove the external crown member 30, the external crown member 30 is lifted upward. Once the opening 421 of the resilient cap 42 disengages from the retention block 41, the removal is complete. Due to the resiliency of the resilient cap 42, without the external crown member 30 being lifted by a predetermined distance, the resilient cap 42 does not separate from the retention block 41. This helps the artificial tooth to resist a pulling force induced by a sticky foodstuff that is being chewed by the tooth and thus, coupling stability between the internal crown members 10 and the external crown member 30 can be greatly improved. Further, the resilient cap can be made of a rubber material or can be a resilient cap made of a metal plate. Further, the retention block is formed on a top surface of the internal crown member.

Figure 9:
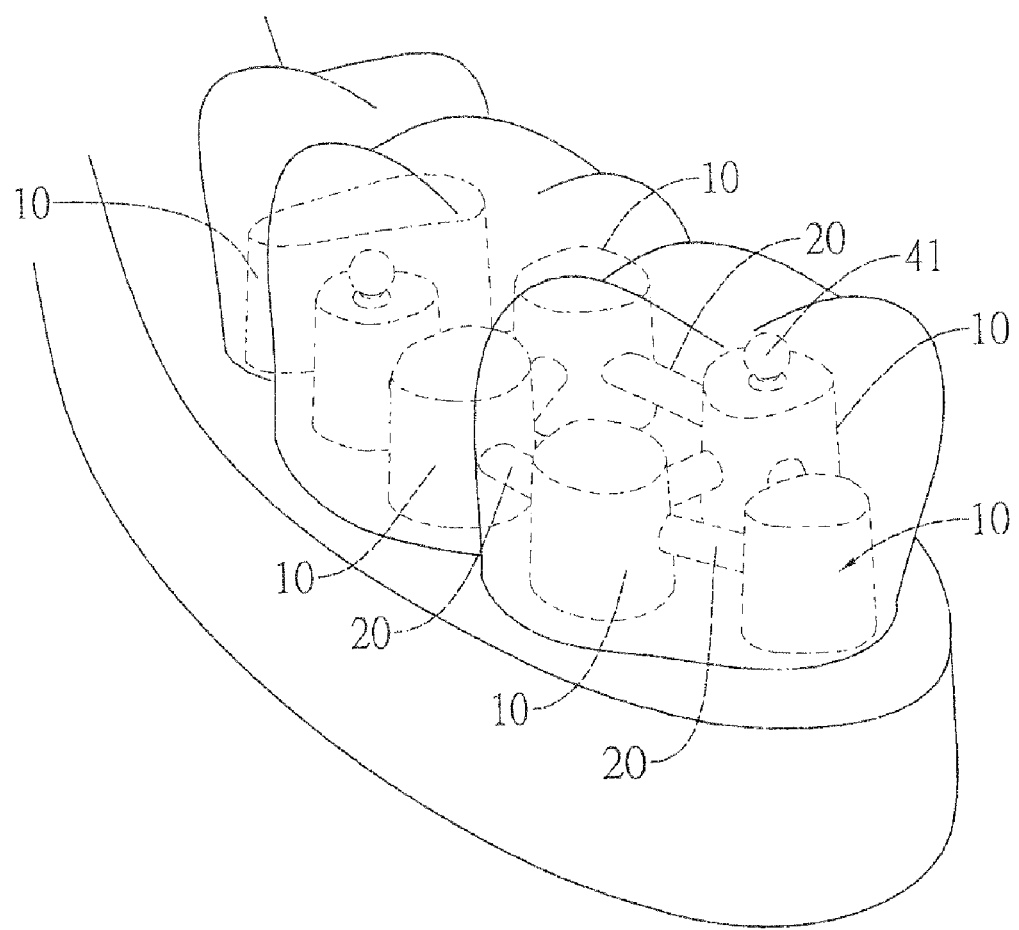
FIG. 9 is a schematic view showing an external crown member coupled to internal crown members according to another embodiment of the present invention.
Figure 10:
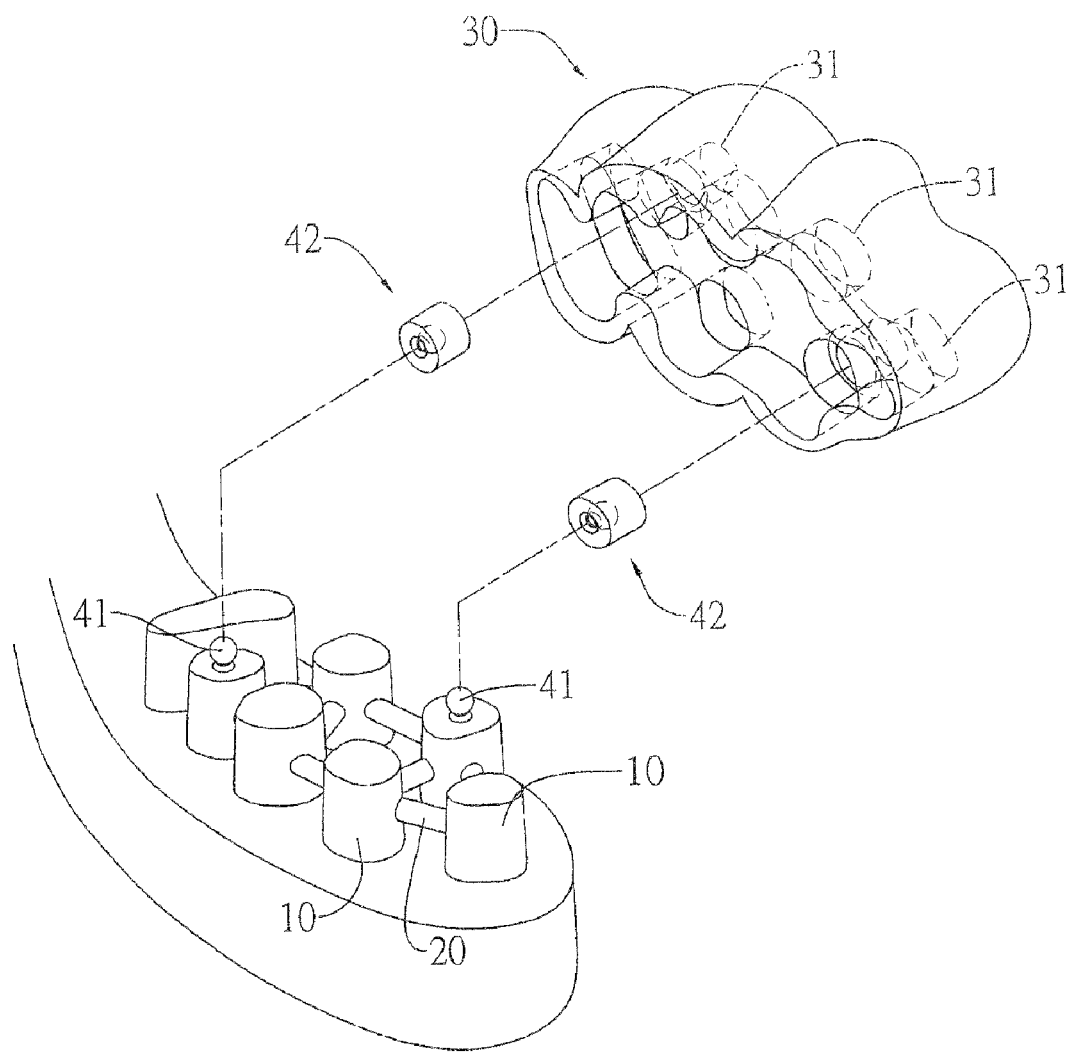
FIG. 10 is a schematic view showing spatial relationship in coupling the external crown member to the internal crown members according to said another embodiment of the present invention.
Figure 11:
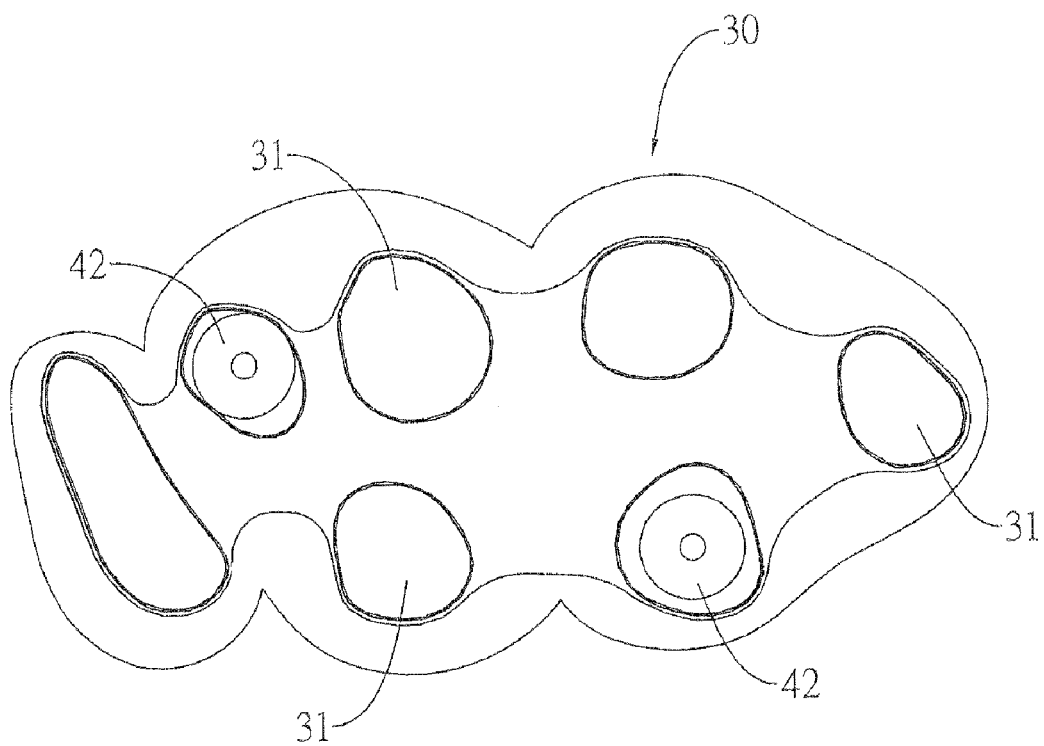
FIG. 11 is a schematic bottom view of the external crown member according to said another embodiment of the present invention.

As shown in FIGS. 9-11, a different structure of the external crown member 30 according to the present invention is provided, which comprises a plurality of tooth combination bodies and is not limited to application to a single natural tooth. Further, the internal crown members 10 can be connected to each other to bear a great force.

The present invention allows a dentist to carry out a throughout treatment, allows a user to easily mount and clean the artificial tooth, and eliminates the problems of accumulation of dirty substance occurring in the conventional devices.

It will be understood that each of the elements described above, or two or more together may also find a useful application in other types of methods differing from the type described above.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the spirit of the present invention.

I claim:

1. An artificial tooth, comprising:
   a plurality of internal crown members, which are respectively adapted to be fitted to a plurality of abutments, the abutments being formed by cutting a single natural tooth;
   a plurality of connection bars, each of which connects to at least two of the internal crown members;
   at least one external crown member, which forms therein at least one recess, the recess being formed to correspond to the internal crown members;

wherein the external crown member, when fit to the internal crown members, is tightly engaged with the internal crown members; and a retention structure, which comprises:
  a retention block, which is of a spherical form and is formed on one of the internal crown members, which are adapted to be correspondingly fitted to said plurality of abutments, and
  a resilient cap, which is formed in one of the at least one recess and including an opening and a fitting chamber formed in communication with each other in said resilient cap, the opening being formed to correspond to the retention block and being smaller than a maximum outside diameter of the retention block, and the fitting chamber being fit over and enclosing an outer circumference of the retention block.

2. The artificial tooth according to claim 1, wherein the resilient cap is made of a rubber material or comprises a cap made of metal plate, the retention block being formed on a top surface of the internal crown member.

3. An artificial tooth, comprising:
  a plurality of internal crown members, which are respectively adapted to be fitted to a plurality of abutments, the abutments being formed by cutting a single natural tooth;
  a plurality of connection bars, each of which connects to at least two of the internal crown members;
  at least one external crown member, which forms therein a plurality of recesses, the recesses being formed to correspond to the internal crown members, the external crown member being of an outer appearance of two teeth; and
  a retention structure, which comprises:
    a retention block, which is of a spherical form and is formed on one of the internal crown members, which are adapted to be correspondingly fitted to said plurality of abutments, and
    a resilient cap, which is formed in one of the recesses and including an opening and a fitting chamber formed in said resilient cap, the opening being in communication with the fitting chamber and being smaller than a maximum outside diameter of the retention block, the opening being formed to correspond to the retention block, the fitting chamber being fit over and enclosing an outer circumference of the retention block.

4. The artificial tooth according to claim 3, wherein the resilient cap is made of a rubber material or comprises a cap made of metal plate, the retention block being formed on a top surface of the internal crown member.

* * * * *